United States Patent
Heuer et al.

(10) Patent No.: US 11,413,072 B2
(45) Date of Patent: Aug. 16, 2022

(54) POLYAXIAL SCREW

(71) Applicant: SILONY MEDICAL INTERNATIONAL AG, Frauenfeld (CH)

(72) Inventors: Frank Heuer, Filderstadt (DE); Christoph Mehren, Munich (DE); Axel Hempfing, Kassel (DE); Lorin M. Benneker, Herrenschwanden (CH)

(73) Assignee: SILONY MEDICAL INTERNATIONAL AG, Frauenfeld (CH)

(*) Notice: Subject to any disclaimer, the term of this patent is extended or adjusted under 35 U.S.C. 154(b) by 0 days.

(21) Appl. No.: 16/962,696

(22) PCT Filed: Jan. 9, 2019

(86) PCT No.: PCT/EP2019/050420
§ 371 (c)(1),
(2) Date: Jul. 16, 2020

(87) PCT Pub. No.: WO2019/149483
PCT Pub. Date: Aug. 8, 2019

(65) Prior Publication Data
US 2020/0352609 A1     Nov. 12, 2020

(30) Foreign Application Priority Data
Jan. 31, 2018 (DE) .................... 10 2018 102 173.9

(51) Int. Cl.
A61B 17/70      (2006.01)
A61B 17/86      (2006.01)

(52) U.S. Cl.
CPC ...... *A61B 17/7037* (2013.01); *A61B 17/7076* (2013.01); *A61B 17/863* (2013.01)

(58) Field of Classification Search
None
See application file for complete search history.

(56) References Cited

U.S. PATENT DOCUMENTS

| | | | | |
|---|---|---|---|---|
| 2008/0234756 | A1* | 9/2008 | Sutcliffe | A61B 17/7037 606/308 |
| 2012/0245640 | A1* | 9/2012 | Auerbach | A61B 17/7037 606/264 |

(Continued)

FOREIGN PATENT DOCUMENTS

| | | |
|---|---|---|
| DE | 102016114266 A1 | 2/2018 |
| EP | 02502594 A1 | 9/2012 |

(Continued)

OTHER PUBLICATIONS

Non-translated German Examination Report, dated Oct. 19, 2018.
(Continued)

*Primary Examiner* — Eduardo C Robert
*Assistant Examiner* — Michelle C Eckman
(74) *Attorney, Agent, or Firm* — George McGuire

(57) ABSTRACT

The invention relates to a polyaxial screw including a screw anchor and a fork head which has two arms, is U-shaped in a lateral view and has a receiving opening for a correction element, and including a pressure piece which can be arranged in the fork head between the head of the screw anchor and the correction element, rests on the head of the screw anchor and can be loaded by the correction element.

21 Claims, 7 Drawing Sheets

(56) References Cited

U.S. PATENT DOCUMENTS

| | | | |
|---|---|---|---|
| 2017/0020576 A1* | 1/2017 | Siccardi | A61B 17/7037 |
| 2017/0181776 A1* | 6/2017 | Beretta | A61B 17/7037 |
| 2019/0274738 A1* | 9/2019 | Heuer | A61B 17/7076 |
| 2019/2747381 | 9/2019 | Heuer | |

FOREIGN PATENT DOCUMENTS

| | | | |
|---|---|---|---|
| EP | 02586392 A1 | 5/2013 | |
| EP | 02638874 A2 | 9/2013 | |
| WO | 2015155702 A1 | 10/2015 | |

OTHER PUBLICATIONS

International Search Report and Non-Translated Written Opinion Form PCT/IS/210 and PCT/ISA/237, International Application No. PCT/EP2019/050420, pp. 1-11, International Filing Date Jan. 9, 2019, mailing date of search report dated May 9, 2019.

\* cited by examiner

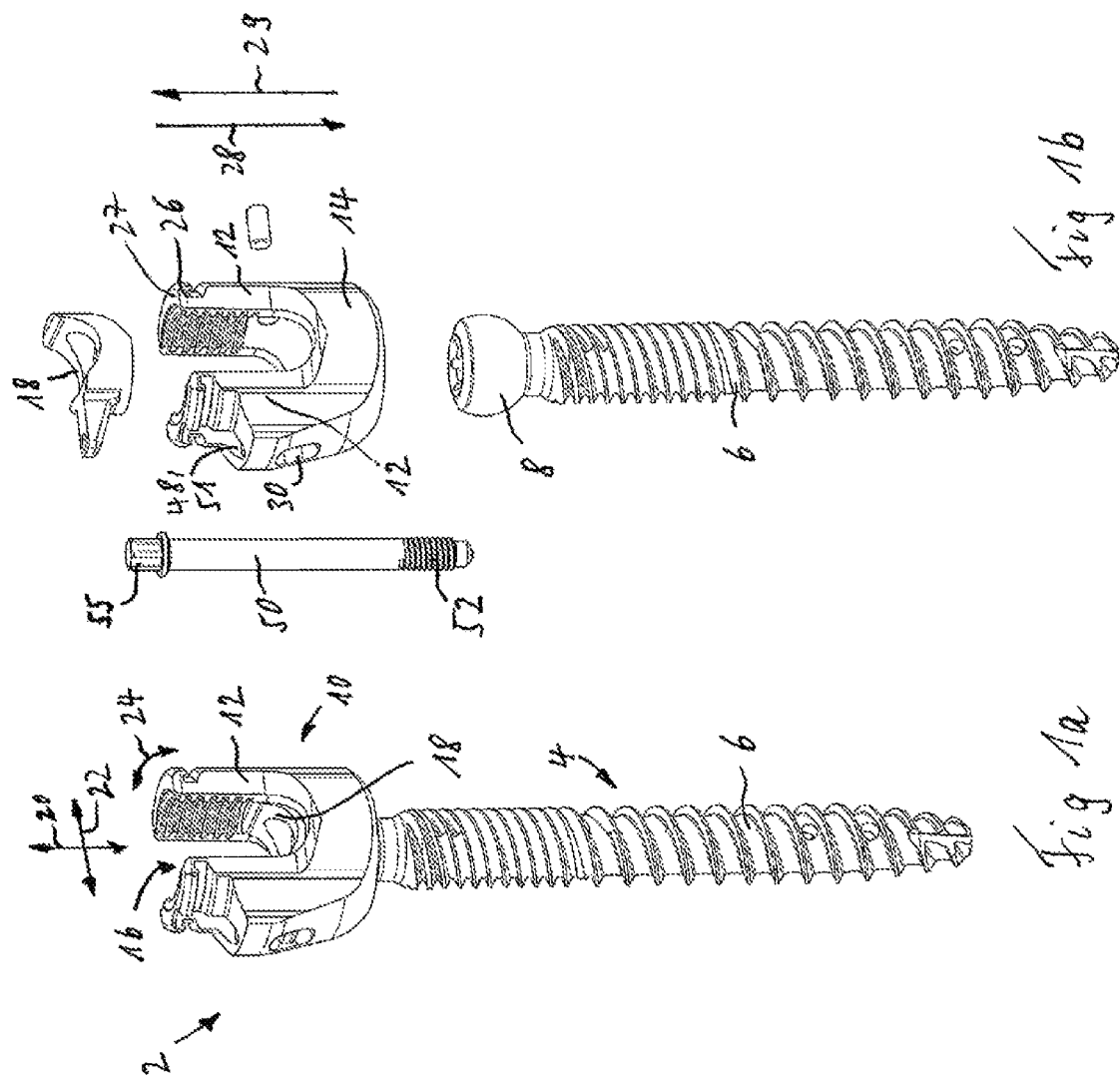

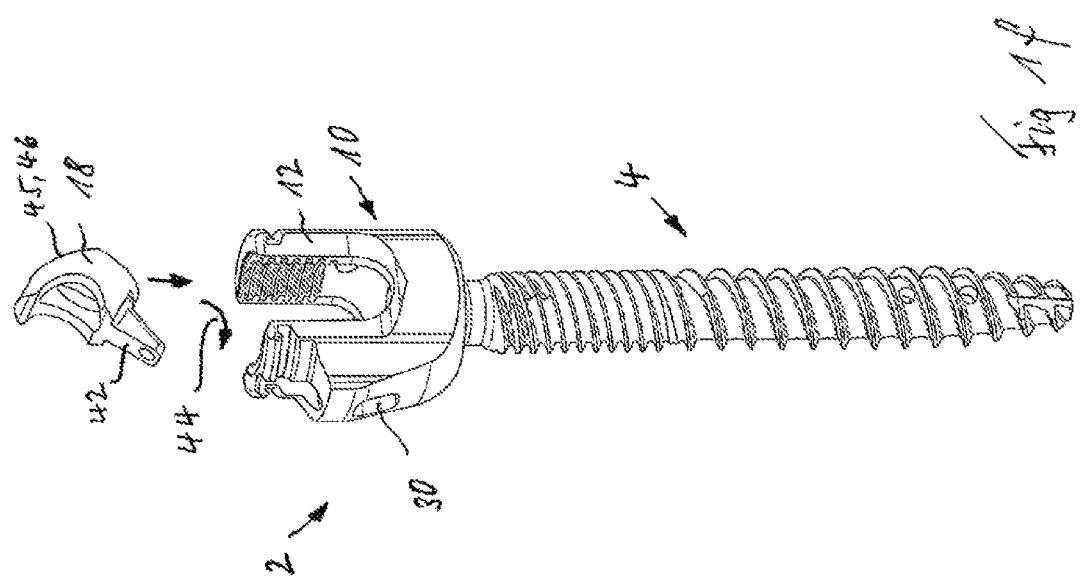

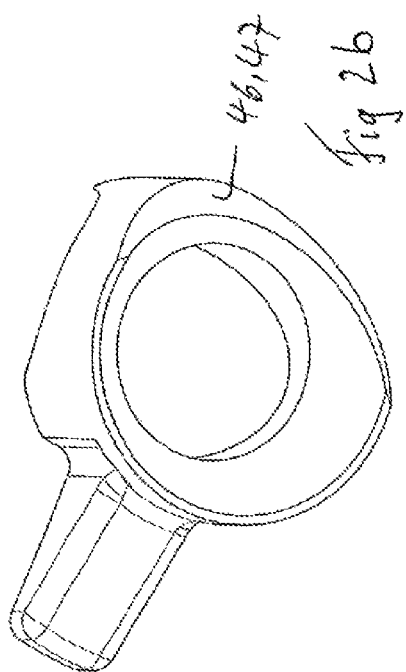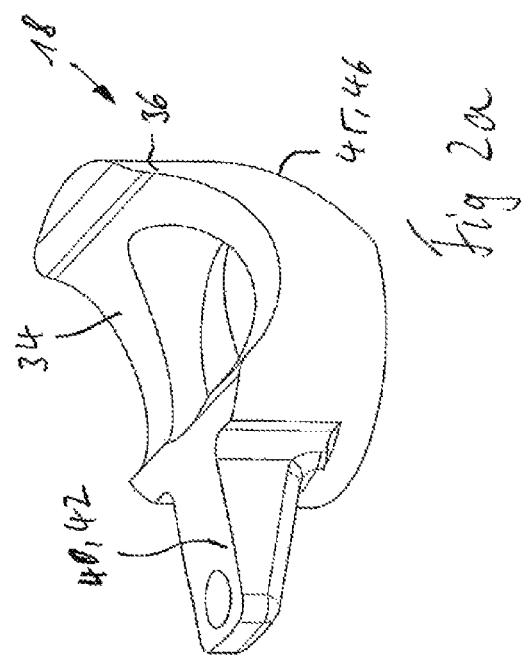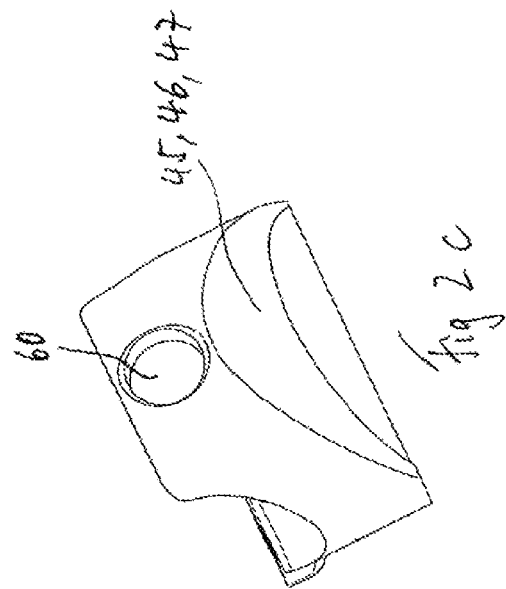

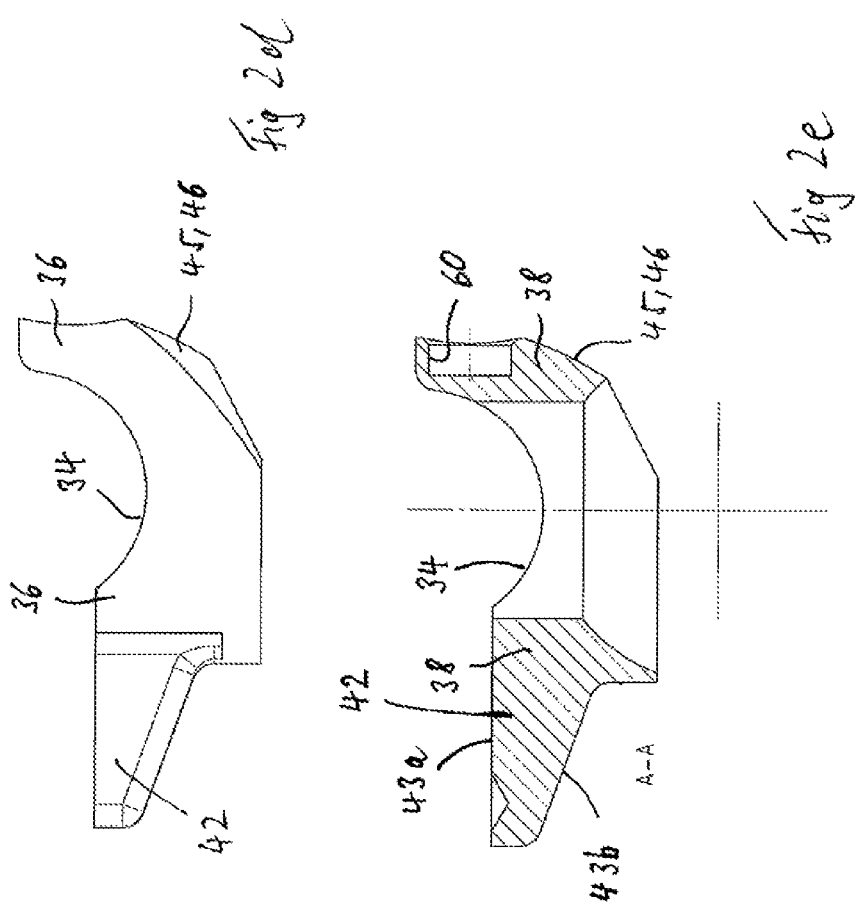

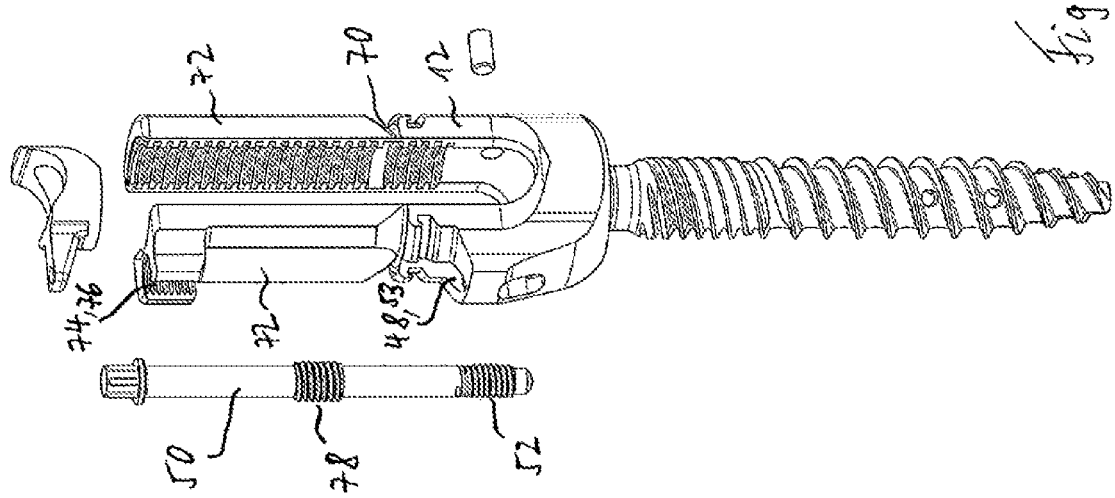
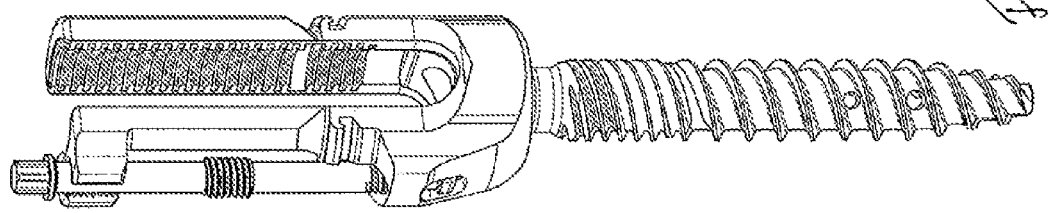
Fig 3b
Fig 3a

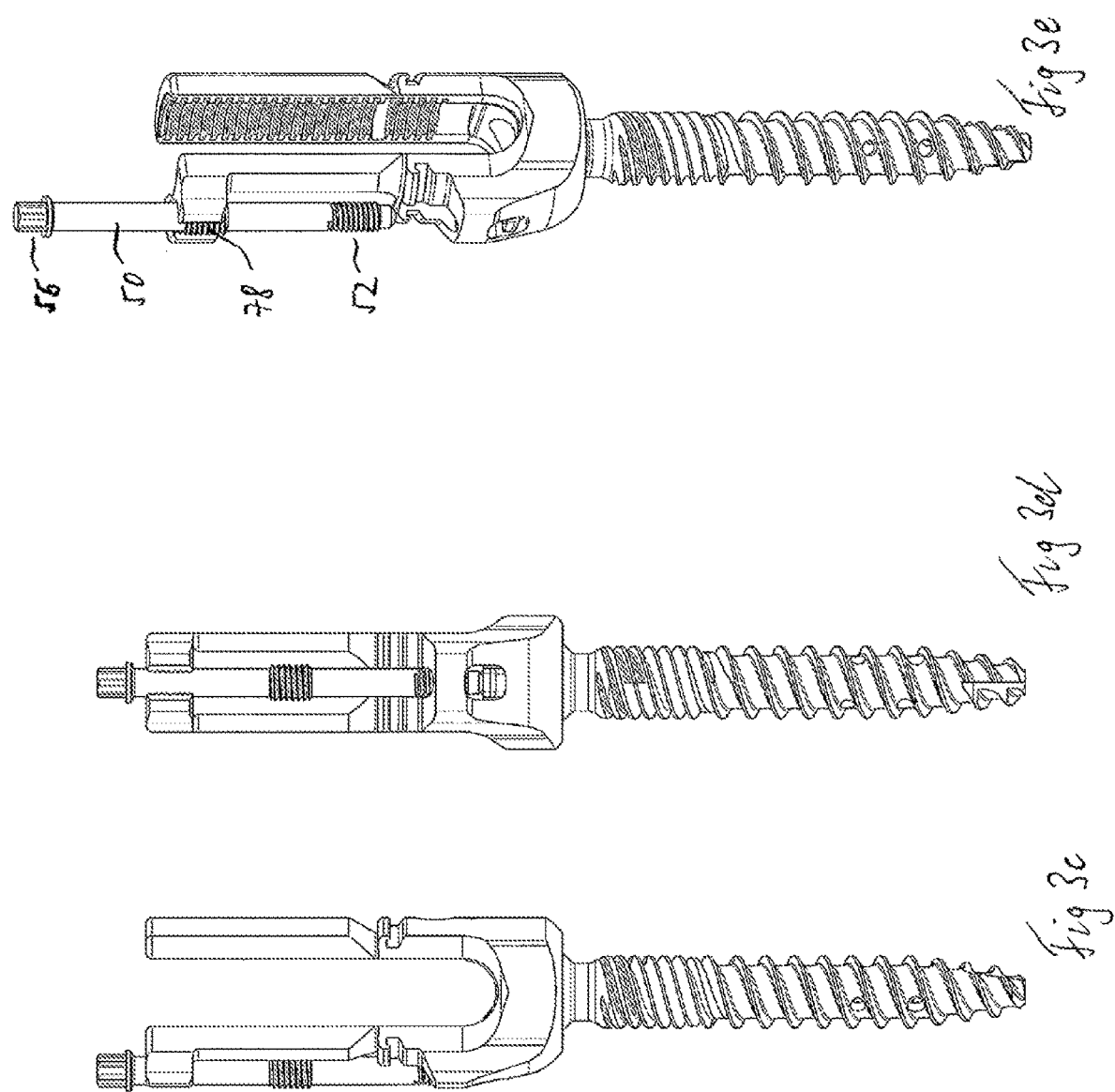

POLYAXIAL SCREW

CROSS-REFERENCE TO RELATED APPLICATION

The present application is the United States National Phase application of PCT Application PCT/EP2019/050420, filed Jan. 9, 2019, which relates and claims priority to German Application No. DE 10 2018 102 173.9 filed Jan. 31, 2018, the entirety of each of which is incorporated herein by reference.

BACKGROUND

Field of Invention

The invention relates to a polyaxial screw, in particular a pedicle screw, comprising a screw anchor which has a threaded shaft and a head, and comprising a fork head which has two arms, is U-shaped in a lateral view and has a receiving opening for a correction element, in particular a correction rod, the fork head having an axial direction, a radial direction in relation thereto and a peripheral direction, and having a distal end adjacent to the screw anchor and a proximal end facing away from said screw anchor in the axial direction, such that a distal direction and a proximal direction are also defined, the head of the screw anchor, when inserted, being mounted in a distal end region of the fork head so as to be polyaxially pivotable, and it being possible for the fork head to be fixed in a pivot position, which is intended by the surgeon, with respect to the head of the screw anchor which is fixed or can be fixed in the bone, the arms extending in the proximal direction proceeding from a distal region of the fork head, ending proximally freely, and between themselves delimiting the receiving opening for the correction element, the arms having a radially outer peripheral region in which at least one holding groove or another instrument attachment point is formed in order to grip the fork head by means of a handling instrument, and the polyaxial screw comprising a pressure piece which can be arranged in the fork head between the head of the screw anchor and the correction element, rests on the head of the screw anchor and can be loaded by the correction element, it being possible for a temporarily acting force to be exerted on the pressure piece by means of the handling instrument acting on the fork head or by means of another actuating element, such that, as a result, the fork head is temporarily non-adjustably held in relation to the head of the screw anchor in a pivot position desired by the surgeon, until the fork head and the screw anchor are permanently fixed against one another by means of a further actuating element, the pressure piece being supported, in the region of an arm of the fork head, against said arm in the axial direction by means of a bearing, and the pressure piece having a receiving region diametrically opposite for an actuating force acting in the axial direction, which actuating force tries to pivot the pressure piece in the distal direction with respect to the bearing, causing the temporarily acting force in the direction of the head of the screw anchor, the fork head having an access hole on one arm, which access hole extends in the axial direction and through which the receiving region of the pressure piece can be accessed by the handling instrument or the other actuating element, said arm of the fork head having a hole which extends from the inside in the radial direction to the outside and into which the receiving region of the pressure piece engages from the inside when said pressure piece is in its intended mounting position.

Prior Art

A polyaxial screw of this kind is the subject matter of the not previously published DE 10 2016 114 266.2 by the applicant. Another polyaxial screw of this kind comprising a pressure piece which is slightly pivotable with respect to a bearing in order to achieve a temporary clamping of the fork head and screw anchor is also known from WO 2015/155702 A1. According to this prior art, the screw anchor is brought into its mounting position together with the pressure piece through a significantly protruding lateral opening. This lateral opening naturally breaches the fork head from the distal end thereof and considerably weakens the fork head.

Proceeding from this prior art, the problem addressed by the present invention is that of designing the fork head to be more stable overall, and of having less installation space available for joining and mounting processes.

SUMMARY OF THE INVENTION

Proceeding from the polyaxial screw mentioned at the outset, this problem is solved according to the invention in that the fork head, in the region of its distal end, has a through-opening for the screw anchor, which through-opening is continuously delimited in the peripheral direction, such that the screw anchor can be inserted into the fork head through said through-opening in the axial direction, and in that the pressure piece has an edge cut-out radially opposite from the receiving region thereof, in a distal end region facing the head of the screw anchor, which edge cut-out is designed such that the receiving region of the pressure piece, when obliquely inclined, can be inserted into the fork head from above in the axial direction and said pressure piece can be pivoted into its intended mounting position, into which the receiving region of the pressure piece engages in the hole, which extends radially outward, and rests on the head of the screw anchor.

Because the screw anchor is inserted through the through-opening in the fork head, which through-opening is closed in the peripheral direction, no protruding transverse opening needs to be formed in the fork head, which would mean a reduction in the stability of the fork head. According to another concept of the invention, the pressure piece comprising the above-mentioned cut-out is designed such that it can be inserted into the fork head from above when obliquely inclined. The pressure piece therefore does not have to be inserted radially through a protruding lateral insertion opening, as in WO 2015/155702 A1 mentioned above. The cut-out therefore serves the purpose that the pressure piece passes inside of the arm when said pressure piece is pivoted into its intended mounting position, i.e. does not collide with a distal cylindrical edge and is not prevented from pivoting in. Only this design makes it possible to mount the pressure piece in the manner claimed, and it has been established that, as a result, the temporary clamping of the fork head, pressure piece and screw anchor is not adversely affected. According to the unpublished DE 10 2016 114 266.2, the pressure piece can also be joined axially; however, it is not obliquely inclined, but rather is inserted into the fork head parallel to the final mounting position thereof. The radially projecting receiving region for the temporary actuating force either slides in a radially inner access opening in one of the arms, or the pressure piece is axially joined so as to be rotated by 90°, such that the receiving region slides down within the U-shape delimited by the arms and is then brought into the mounting position by rotating the pressure piece back in a radially inner peripheral groove in one of the arms. However, both this radially inner peripheral groove and the above-mentioned radially inner axial access opening formed on an arm weaken the relevant arm. Both can be dispensed with in the present development of the polyaxial pedicle screw according to the invention. It is only necessary to provide one hole extending from the inside to the outside in the radial direction for the radially projecting receiving region of the pressure piece. Said hole only has to be slightly larger than the radially projecting receiving region of the pressure piece so that the pressure piece as described above can be pivoted into the intended mounting position during the axial joining.

In a development of the solution according to the invention, it is particularly advantageous if the two arms of the fork head delimit an in particular concentric interior and the pressure piece is designed to have an in particular concentric periphery corresponding to the interior, except for its receiving region for the actuating force and except for the cut-out. This means that the pressure piece is also axially guided through the interior of the fork head. The pressure piece can also be arranged so as to have little play in the interior, such that it can pivot in relation to the bearing in the course of the temporary fixing. With the exception of its radially projecting receiving region for the temporary clamping force, the pressure piece is therefore received as in a pot in the fork head and is adapted to the inner shape of this pot.

It is advantageous if the cut-out is only just dimensioned such that the pressure piece can be pivoted into the final mounting position during axial insertion. For this purpose, it is advantageous if the cut-out is delimited by an outwardly convex surface or by faceted surface segments. These faceted surface segments can also each be flat, but be interconnected such that an approximately curved delimiting surface is created.

It can be advantageous in terms of manufacturing if the hole, which extends from the inside radially outward and into which the radially projecting receiving region of the pressure piece engages, passes through the arm of the fork head and opens at the outer periphery of the arm. As a result, the lever arm which is formed by the radially projecting receiving region of the pressure piece can be extended in order to produce the temporary clamping. A reduction in stability that is relevant in practice can be completely excluded if the opening tapers from the radial inside to the radial outside. In a development of this concept, it is particularly advantageous if the hole which extends from the inside to the radial outside is delimited by a distal flank which is inclined in the proximal direction from the inside to the outside. In particular, a proximal flank which delimits the hole can be formed so as to be orthogonal to the axial direction. The inclination of the distal flank results in an increase in the pivoting space for the radially projecting receiving region of the pressure piece when pivoted into the mounting position.

It is particularly advantageous if the receiving region of the pressure piece, which extends radially outward, is thicker radially inward in the axial direction than radially further outward, or in other words if it tapers radially outward. Due to the material reinforcement further inside, the lever of the pressure piece is strengthened when the temporary actuating force is exerted, and the applied actuating force is more effectively applied to the pressure piece and converted into an axial clamping force on the head of the screw anchor.

It is also advantageous if the receiving region, which extends radially outward, has a flank which extends orthogonally to the longitudinal direction proximally and a flank which is inclined obliquely to the longitudinal direction.

The access hole to the receiving region of the pressure piece, which access hole extends in the axial direction, mentioned at the outset, is preferably designed as an axial opening which is continuously delimited in its peripheral direction. In this way, the access hole can perform a guide function for a pin-shaped actuating element.

The access hole is preferably designed and arranged on an arm of the fork head, such that a pin-shaped actuating element of a handling instrument which grips the fork head can engage in the axial access hole and can apply force to the receiving region of the pressure piece in the axial direction.

However, it can also be particularly advantageous if the access hole has an internal thread, into which a pin-shaped actuating element having an external thread can be screwed and the free end of which can apply force to the receiving region of the pressure piece in the axial direction. As a result, the temporary clamping force can be exerted independently of a handling instrument gripping the fork head. It therefore has been shown to be particularly advantageous if the pin-shaped actuating element is designed as a component separate from a handling instrument gripping the fork head and has a tool attachment point. This allows the temporary fixing without having to fix a handling instrument to the fork head at the same time. This is advantageous in particular in the case of complex surgical procedures, such as in the treatment of deformities, such as scoliosis, where a large number of pedicle screws regularly have to be set at a small distance between one another. In this case, a large number of handling instruments projecting outward from the patient would interfere with the surgical care of a specific location. Therefore, it is advantageous if the handling instrument for the fork head can be disconnected and the intended pivot position of the fork head can still remain temporarily fixed by means of the pin-shaped actuating element, which has not yet been achieved using other known pedicle screws to the best of our knowledge.

The invention is also advantageous in conjunction with long-head screws, in the case of which the two arms of the fork head each have a distal arm portion that can be separated at a predetermined breaking point, by means of which arm portion the fork head is, to a certain extent, extended in the axial direction. When implementing the invention on long-head screws of this kind, it is advantageous if a distal arm portion has a second access hole which is aligned with the axial access hole and through which the pin-shaped actuating element can pass. In a further development of this concept, it is advantageous if both access holes which are aligned with one another have an internal thread and, in particular, the pin-shaped actuating element has two external thread portions which are mutually spaced in the axial direction, which, according to a further preferred embodiment, have a lesser distance between one another than the internal thread of the axial access holes. The proximally arranged external thread portion of the pin-shaped actuating element then has the task of fixing the actuating element to the distal arm portion by screwing into the distal internal thread when in the non-active state, i.e. after the temporary clamping has been released. After all surgical fixing measures have been carried out, the relevant arm together with the pin-shaped actuating element held thereon can then be separated from the remaining fork head at the predetermined breaking line.

According to a further embodiment, it is advantageous if the internal thread in the detachable arm portion delimits a larger clear passage opening than an outer diameter in the distal external thread portion of the pin-shaped actuating element, such that the distal external thread portion of the pin-shaped actuating element can be axially inserted translationally through the internal thread in the detachable arm portion.

It is very particularly advantageous that the arm of the fork head, in which the access hole is formed, is thickened in the radial direction in relation to the other arm. This provides material for forming and delimiting the access hole in the arm; this also increases the overall stability of the fork head.

As mentioned at the outset and as also described in the previously unpublished publication, it is advantageous if the bearing has a pin element or shaft element inserted into the fork head in order to pivotably arrange the pressure element, which pin element or shaft element preferably extends in a plane which is orthogonal to the axial direction of the fork head and is inserted into the fork head and against which the pressure piece is supported in the axial direction.

According to a preferred embodiment, the bearing is formed by a free end of a pin element which is inserted through an arm of the fork head from the outside to the radially inside. The pin element is expediently mounted on the fork head only after the pressure piece has been inserted and pivoted into its mounting position. It would be conceivable for the pressure piece to be supported only from below, i.e. against a distal side of the bearing. This also makes it possible for the pressure piece to function as a clamping lever, to a certain extent. The temporary actuating force acting on the receiving region of the pressure piece in the axial direction is increased according to the principles of levers, for example as in a nutcracker having two clamping arms. The pressure piece is supported on the bearing from below, i.e. against the distal side of the bearing, and presses on the head of the screw anchor from above.

Furthermore, it can be advantageous if the free end of the mentioned pin element, which forms the bearing, engages, at least in the axial direction, with play in a radial opening of the pressure piece, which opening is relatively larger. As a result, the pressure piece is held in the fork head securely with respect to all directions; in particular, it can be attached to the fork head before the screw anchor is mounted. On the other hand, the play in the axial direction means that, during the final permanent fixing, the pressure piece can be detached from its axial contact with the bearing by means of a further actuating element, such as a set screw which is screwed into the fork head, and can be optimally supported against the head of the screw anchor under the effect of the final clamping force.

For this purpose, it is advantageous in particular if the pressure piece has an axial play in the region of the bearing and relative to the bearing, such that the pressure piece can carry out an axial actuating movement in the axial direction by means of the correction element when force is applied, without this actuating movement being impeded by the bearing.

It is also advantageous if a clamping force between the pressure piece and the head of the screw anchor, which is generated by applying force to the receiving region of the pressure piece, is less than a clamping force which is generated by applying force by means of the further actuating element. In such a case, the pressure piece can assume its optimal position in relation to the head of the screw anchor when finally permanently fixed by the further actuating element.

BRIEF DESCRIPTION OF THE DRAWINGS

Further features, advantages and details of the invention can be found in the appended claims and the drawings and the following description of preferred embodiments of the polyaxial screw according to the invention. In the drawings:

FIG. 2 *a-e* show different views of the pressure piece of the polyaxial screw according to FIG. 1;

FIG. 3 *a-e* show different views of another embodiment of a polyaxial screw according to the invention and the components thereof, including a pin-shaped means for exerting a temporary clamping between the fork head and screw anchor.

DETAILED DESCRIPTION

Figure 1E:
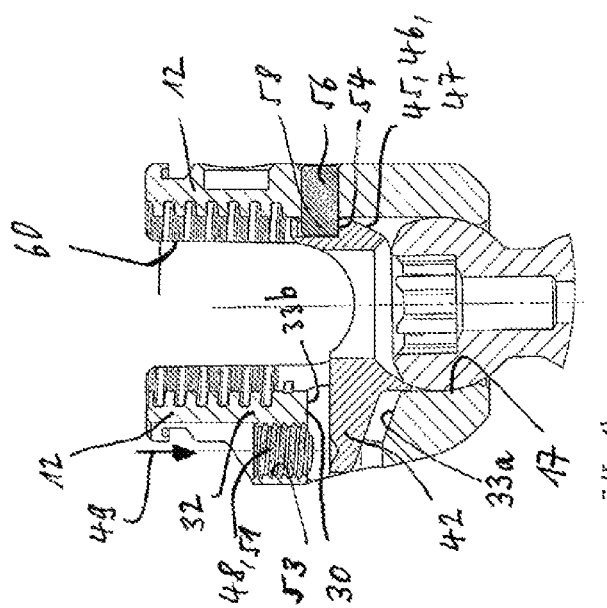
FIG. 1 *a-f* show different views of an embodiment, according to the invention, of a polyaxial screw and the components thereof.
Figure 1D:
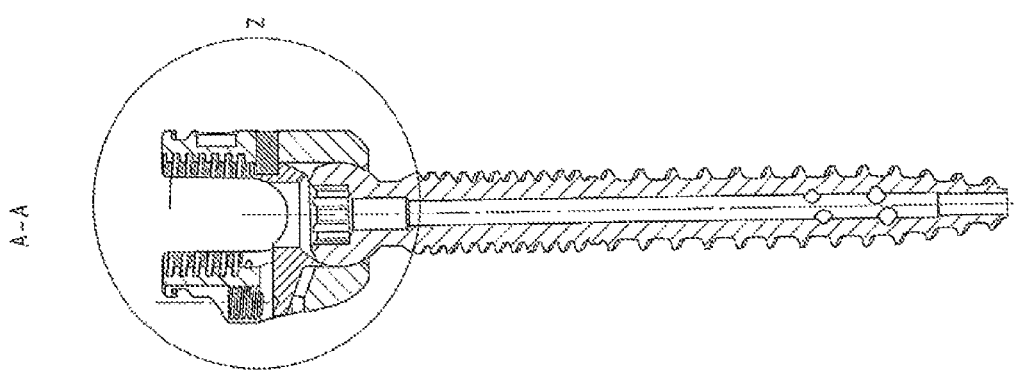
Figure 1C:
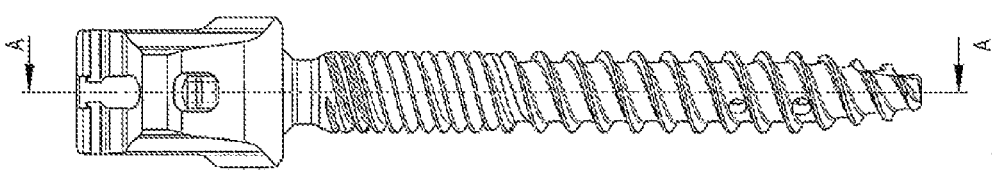

FIG. 1*a-f* show a polyaxial screw 2 according to the invention in the form of a pedicle screw. The pedicle screw comprises a screw anchor 4 which has a threaded shaft 6 and a head 8, and comprises a fork head 10 which has two arms 12 which, proceeding from a distal end region 14 of the fork head 10, extend in the proximal direction, i.e. away from the screw anchor 4, and end freely. Said arms delimit a U-shaped receiving opening 16 for a pressure piece 18 and a correction element (not shown), in particular a correction rod, which is inserted into the receiving opening 16 in a manner known per se and connects adjacent or, optionally, a plurality of pedicle screws to one another. The fork head 10 has, at the distal end region 14, a through-opening 17 which is continuously delimited in the peripheral direction, such that the screw anchor 2 can be inserted into the fork head 10 through this through-opening 17 in the longitudinal direction. In the inserted state, the head 8 of the screw anchor 4 is mounted in the distal end region 14 of the fork head 10 so as to be polyaxially pivotable. When a sufficient force is exerted on the pressure piece 18 in the direction of the head 8, the fork head 10 can be set so as to be immovable in relation to the head 8 of the screw anchor as a result of the clamping action produced, which will be explained in detail below. The fork head 10 furthermore defines an axial direction 20, a radial direction 22 in relation thereto and a peripheral direction 24, and the distal end region 14 and a proximal end region 26 and a proximal end 27. A distal direction 28 and a proximal direction 29 are thus also provided.

An arm 12 of the fork head 10 has, on its inner side, a hole 30 which extends outward, approximately orthogonally to the axial direction 20 in the radial direction 22. In the case illustrated by way of example, the hole 30 extends through a wall region 32 of the arm 12 and opens into the outer periphery of the arm 12. The hole is designed to taper radially outward by being delimited by a distal flank 33*a* which is inclined from the inside to the outside in the proximal direction 29. A proximal flank 33*b* extends orthogonally to the axial direction 20.

As can be seen from the illustration of the pressure piece 18 in FIG. 2*a-e*, the pressure piece 18 comprises an approximately half-shell-shaped receptacle 34 for a rod-shaped correction element. This half-shell-shaped receptacle 34 is laterally delimited by wall portions 36 which extend in the proximal direction and which lie opposite one another and extend in the proximal direction proceeding from an annular, closed base portion 38 of the pressure piece 18. Proceeding from one of the wall portions 36, an extension or projection 40 extends outward in the radial direction 22. This extension or projection 40 forms a receiving region 42 for an actuating force which acts in the axial direction 20 and is exerted on the pressure piece 18 in a manner to be described, in order to produce a temporary clamping between the fork head 10 and the screw anchor 4. The receiving region 42 has proximally a flank 43a which extends orthogonally to the axial direction 22, and distally has a flank 43b which is inclined obliquely to the axial direction 22.

Proceeding from the oblique orientation of the pressure piece 18 in relation to the axial direction 20, which orientation is shown in FIG. 1f, the pressure piece 18 can be inserted into the fork head 10 in the axial direction 20, and then pivot, in the direction of the indicated arrow 44, into the mounting position shown in the remaining figures, the receiving region 42 increasingly engaging in the aforementioned hole 30. This axial joining of the pressure piece 18 in an obliquely inclined state with the receiving region 42 thereof at the front and the final pivoting of the pressure piece 18 into its mounting position is possible because the pressure piece 18, on the side which is opposite the receiving region 42, in a distal end region 45 which faces the head 8 of the screw anchor 2, has a cut-out 46 which is designed such that the distal end region 45 does not collide with the inner contour of the fork head 10 and the arms 12 during the axial insertion and pivoting of the pressure piece 18, and is not blocked as a result. As mentioned at the outset, the cut-out 46 serves precisely this purpose. Since the fork head 10 can typically be concentric on the inside, it is sufficient if the cut-out is delimited by a surface 47 which is outwardly convex. However, the cut-out could also be delimited by, in particular, a plurality of in particular planar surface segments arranged so as to be faceted.

As shown in FIG. 1a, b-e, the receiving region 42 of the pressure piece 18 protrudes into the hole 30 which opens radially outward, such that a free end of the receiving region 42 is exposed in order to receive an actuating force which acts in the axial direction, which is indicated in FIG. 1e by an arrow 49.

It can also be seen that the relevant arm 12 of the fork head 10 has an access hole 48 which extends in the axial direction 20 and permits access to the radially outwardly opening hole 30 in which the receiving region 42 of the pressure piece 18 lies. The access hole 48 is designed as an axial opening 51 which is continuously delimited in the peripheral direction. Thus, an actuating force can be exerted on the receiving region 42 of the pressure piece 18, in the direction of arrow 49 in FIG. 1e, through this access hole 48 by means of a pin-shaped actuating element of a handling instrument which holds the pedicle screw or, as shown, another actuating element 50 (FIG. 1b). In the simplest case, the actuating element 50 can be designed as a pin or plunger, which passes through the access hole 48 translationally in the axial direction 20 and is axially supported against the receiving region 42 of the pressure piece. However, the actuating element 50 can also have an external thread portion 52, by means of which said actuating element can be screwed into an internal thread 53 in the access hole 48, such that the actuating force exerted on the receiving portion 42 can be adjusted. In such a case, the actuating element 50 preferably also has a tool attachment point 55.

The pressure piece 18 is designed, on its side which is diametrically opposite the extension or projection 40, which forms the actuating force for the receiving region 42, such that said pressure piece can be axially supported on a bearing 54 on the other arm 12 of the fork head 10, in such a way that the pressure piece 18 can be pivoted in the direction of the head 8 of the screw anchor 4 in a plane including the axial direction 20 when force is applied in the direction of the arrow 49.

This bearing 54 is produced, by way of example, in that a pin element 56 is inserted, in particular pressed in, from the outside radially inward through an opening corresponding to the pin element in the arm of the fork head, such that the radially inner free end 58 of the pin element 56 forms the bearing 54. For this purpose, the free end 58 engages in a relatively larger radial opening 60 in the pressure piece 18. This engagement is subject to play at least in the axial direction 20, which can also be seen from FIG. 1e. For this purpose, the radial opening 60 is elongate or oval in the axial direction 20. When the temporary actuating force is applied in the direction of arrow 49 to the receiving region 42, the pressure piece 18 is supported within its opening 60 from below, i.e. against the distal side of the free end 58 of the pin element 56, as a result of which the pressure piece exerts force on the head eight of the screw anchor in the axial direction 20 and thus causes the temporary clamping. After the temporary actuating force in the direction of arrow 49 has been removed or during this temporary clamping, a further actuating element, in particular a set screw (not shown), which is known per se, can be screwed into an internal thread 60 of the arms 12 of the fork head 10 and exert the final clamping pressure to the pressure piece 18 in the axial direction 20 by means of the previously inserted correction rod. The pressure piece can be detached from the support on the bearing 54 in the axial direction due to the aforementioned play and can assume its final optimal clamping position in relation to the head of the screw anchor.

FIGS. 3a-e show a further embodiment of the polyaxial screw according to the invention, which is designed in this case as a long shaft screw. The two arms 12 each have a distal arm portion 72 that can be separated at a predetermined breaking point 70. One of the distal arm portions 72 has an opening 74 which is aligned with the axial access hole 48, such that the pin-shaped actuating element 50 can also pass through this second opening 74. Advantageously and by way of example, both the access hole 48 and the second opening 74 each have an internal thread 53 and 76, respectively. However, the second opening 74 and its internal thread 76 are open at the edge, i.e. they are C-shaped in the axial direction, as a result of which installation space is saved in the radial direction. The pin-shaped actuating element 50 also has a distal external thread portion 52 and a further proximal external thread portion 78. The internal thread 76 has a slightly larger diameter than the internal thread 53, such that the distal external thread portion 52 of the pin-shaped actuating element 50 can be inserted translationally through the internal thread 76. However, the distance between the external thread portions 52, 78 is preferably less than the distance between the internal threads 53, 76. This makes it possible that the pin-shaped actuating element can be brought into the retracted position shown in FIG. 3e, in which position the distal external thread portion 52 is freed from the internal thread 53 of the access hole 48; however, the proximal external thread portion 78 of the pin-shaped actuating element 50 is held in the internal thread 76 of the separable arm portion 72 and can be separated, together with this arm portion, from the fork head.

The invention claimed is:

1. A polyaxial screw, comprising a screw anchor which has a threaded shaft and a head, and comprising a fork head which has two arms, is U-shaped in a lateral view and has a receiving opening for a correction element, the fork head having an axial direction, a radial direction in relation thereto and a peripheral direction, and having a distal end adjacent to the screw anchor and a proximal end facing away from said screw anchor in the axial direction, such that a distal direction and a proximal direction are also defined, the head of the screw anchor, when inserted, being mounted in a distal end region of the fork head so as to be polyaxially pivotable, and it being possible for the fork head to be fixed in a pivot position, which is intended by the surgeon, with respect to the head of the screw anchor which can be fixed in the bone, the arms extending in the proximal direction proceeding from the distal region of the fork head, ending proximally freely, and between themselves delimiting the receiving opening for the correction element, the arms having a radially outer peripheral region in which at least one holding groove or another instrument attachment point is formed in order to grip the fork head by means of a handling instrument, and the polyaxial screw comprising a pressure piece which can be arranged in the fork head between the head of the screw anchor and the correction element, and the correction element rests on the pressure piece which rests on the screw anchor and the pressure piece can be loaded by the correction element, it being possible for a temporarily acting force to be exerted on the pressure piece by means of one of the handling instrument acting on the fork head or by means of another actuating element, such that, as a result, the fork head is temporarily non-adjustably held in relation to the head of the screw anchor in a pivot position desired by the surgeon, until the fork head and the screw anchor are permanently fixed against one another by means of the another actuating element, the pressure piece being supported, in a region of a first arm of the two arms of the fork head, against said first arm in the axial direction by means of a bearing, and the pressure piece having a receiving region diametrically opposite for an actuating force acting in the axial direction, which actuating force tries to pivot the pressure piece in the distal direction with respect to the bearing, thus causing the temporarily acting force in the direction of the head of the screw anchor, the fork head having an access hole on a second arm of the two arms of the fork head, which access hole extends in the axial direction and through which the receiving region of the pressure piece can be accessed by the handling instrument or the another actuating element, said second arm of the fork head having a hole which extends from an inside in the radial direction to an outside and into which the receiving region of the pressure piece engages from the inside when said pressure piece is in an intended mounting position, characterized in that the fork head, in the distal end region, has a through-opening for the screw anchor, which through-opening is continuously delimited in the peripheral direction, such that the screw anchor can be inserted into the fork head through said through-opening in the axial direction, and in that the pressure piece has a cut-out radially opposite from the receiving region thereof, in a distal end region which faces the head of the screw anchor, which cut-out is designed such that the receiving region of the pressure piece can be inserted into the fork head in the axial direction from above when obliquely inclined, and pivoted into the intended mounting position, in which the receiving region of the pressure piece engages into the hole, which extends radially outward, and rests on the head of the screw anchor.

2. The polyaxial screw according to claim 1, characterized in that the two arms of the fork head delimit an interior, and in that the pressure piece is designed to have a concentric periphery corresponding to the interior, except for the receiving region for the actuating force and the cut-out.

3. The polyaxial screw according to claim 1, characterized in that the cut-out is delimited by an outwardly convex surface.

4. The polyaxial screw according to claim 1, characterized in that the hole which extends from the inside to the outside passes through the arm of the fork head and opens out at an outer periphery of the second arm of the fork head, and tapers from the inside to the outside.

5. The polyaxial screw according to claim 1, characterized in that the hole which extends from the inside to the outside is delimited by a distal flank which is inclined from the inside to the outside in the proximal direction.

6. The polyaxial screw according to claim 1, characterized in that the receiving region of the pressure piece, which receiving region extends to the outside, is thicker on the inside in the axial direction than radially further out.

7. The polyaxial screw according to claim 1, characterized in that the receiving region which extends to the outside proximally has a flank which extends orthogonally to the axial direction and distally has a flank which is obliquely inclined to the axial direction.

8. The polyaxial screw according to claim 1, characterized in that the access hole to the receiving region of the pressure piece is designed as an axial opening which is continuously delimited in the peripheral direction thereof.

9. The polyaxial screw according to claim 1, characterized in that the axial opening is designed and arranged on the second arm of the fork head, such that a pin-shaped actuating element of the handling instrument gripping the fork head can engage in the axial opening and can apply force to the receiving region of the pressure piece in the axial direction.

10. The polyaxial screw according to claim 9, characterized in that the fork head is designed as an elongate head and the two arms have a distal arm portion which can be separated at a predetermined breaking point, and in that the distal arm portion has a second opening which is aligned with the axial opening, through which opening a pin-shaped actuating element can pass.

11. The polyaxial screw according to claim 10, characterized in that the axial opening and the second opening are mutually aligned openings that have an internal thread.

12. The polyaxial screw according to claim 11, characterized in that the pin-shaped actuating element has two external threaded portions which are mutually spaced in the axial direction and preferably have a lesser distance between one another than the internal threads of the mutually aligned openings.

13. The polyaxial screw according to claim 12, characterized in that the internal thread of the second opening of the distal arm portion delimits a larger through-opening than an outer diameter for distal external threaded portion of the two external threaded portions of the pin-shaped actuating element, such that the distal external threaded portion of the pin-shaped actuating element can be pushed axially through the internal thread of the second opening of the distal arm portion.

14. The polyaxial screw according to claim 9, characterized in that the axial access hole carries an internal thread into which the pin-shaped actuating element carrying an external thread portion can be screwed and of which the free end can apply force to the receiving region of the pressure piece in the axial direction.

15. The polyaxial screw according to claim 14, characterized in that the pin-shaped actuating element is designed as a component which is separate from the handling instrument that grips the fork head, and has a tool attachment point.

16. The polyaxial screw according to claim 1, characterized in that the second arm of the fork head, in which the access hole is formed, is thickened in the radial direction in relation to the first arm.

17. The polyaxial screw according to claim 1, characterized in that the bearing has one of a pin element or shaft element which is inserted into the fork head, extends in a plane orthogonally to the axial direction of the fork head and is inserted into the fork head and against which the pressure piece is supported in the axial direction.

18. The polyaxial screw according to claim 1, characterized in that the bearing is formed by a free end of a pin element which is inserted from the outside to the inside by the first arm of the fork head.

19. The polyaxial screw according to claim 18, characterized in that the pin element with its free end engages with play in a relatively larger radial opening of the pressure piece at least in the axial direction.

20. The polyaxial screw according to claim 1, characterized in that the pressure piece has an axial play in a region of the bearing and relative to the bearing, such that the pressure piece, when force is applied in the axial direction, can carry out an axial actuation movement by means of the correction element without said actuation movement being impeded by the bearing.

21. The polyaxial screw according to claim 1, characterized in that a clamping force between the pressure piece and the head of the screw anchor, which is generated by applying force to the receiving region of the pressure piece, is less than a clamping force which is generated by applying force by means of the another actuating element.

* * * * *